United States Patent [19]

Crep

[11] 3,978,528

[45] Sept. 7, 1976

[54] BONE AND JOINT PROSTHESIS

[75] Inventor: John Anthony Crep, West Nyack, N.Y.

[73] Assignee: Howmedica, Inc., New York, N.Y.

[22] Filed: June 26, 1975

[21] Appl. No.: 590,722

[52] U.S. Cl. .................................. 3/1.91; 3/1.912; 128/92 C
[51] Int. Cl.² .......................................... A61F 1/24
[58] Field of Search ........................ 3/1, 1.9–1.913; 128/92 C, 92 CA

[56] References Cited
UNITED STATES PATENTS

| | | | |
|---|---|---|---|
| 2,781,758 | 2/1957 | Chevalier | 128/92 CA |
| 3,694,820 | 10/1972 | Scales et al. | 3/1.91 |
| 3,698,017 | 10/1972 | Scales et al. | 3/1.912 |
| 3,815,157 | 6/1974 | Skorecki et al. | 3/1.91 |
| 3,848,272 | 11/1974 | Noiles | 3/1.913 |

FOREIGN PATENTS OR APPLICATIONS

| | | | |
|---|---|---|---|
| 1,047,640 | 7/1953 | France | 128/92 C |
| 1,362,187 | 7/1974 | United Kingdom | 3/1.91 |

Primary Examiner—Ronald L. Frinks
Attorney, Agent, or Firm—Connolly and Hutz

[57] ABSTRACT

This application describes a shoulder prosthesis having a metal humeral cup component with an extending stem for insertion into the intramedullary canal of the humerus bone. The shoulder or intracancellous component has a ball embraced within the cup between a pair of ultra high molecular weight polyethylene lining inserts, which are locked within the cup under a strong resilient plastic lock ring, which snaps into a circular groove about the rim of the cup. The mouth of the cup and lock ring have mutually engaging bevelled surfaces. The ball and attached scapular component freely pivot or articulate within the cup and lining inserts.

14 Claims, 8 Drawing Figures

U.S. Patent  Sept. 7, 1976  3,978,528
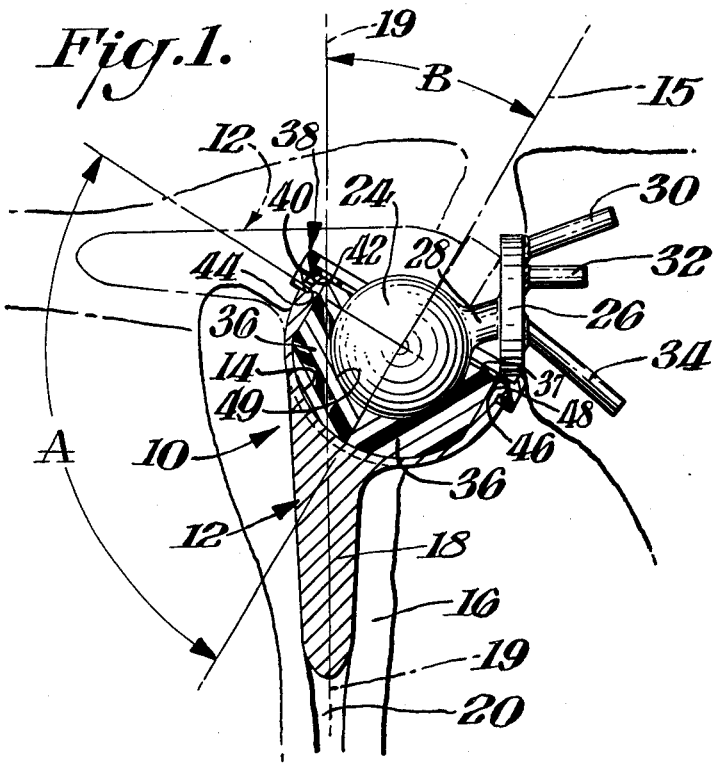
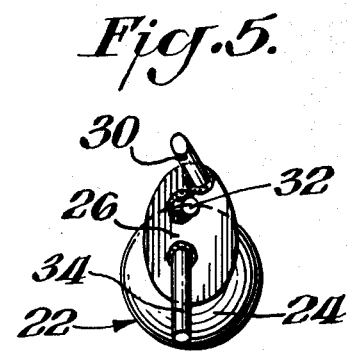
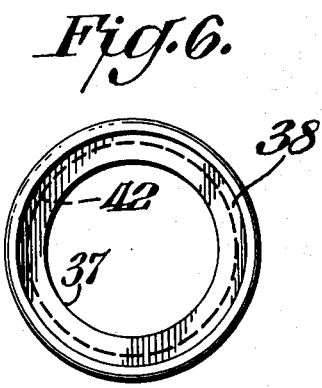
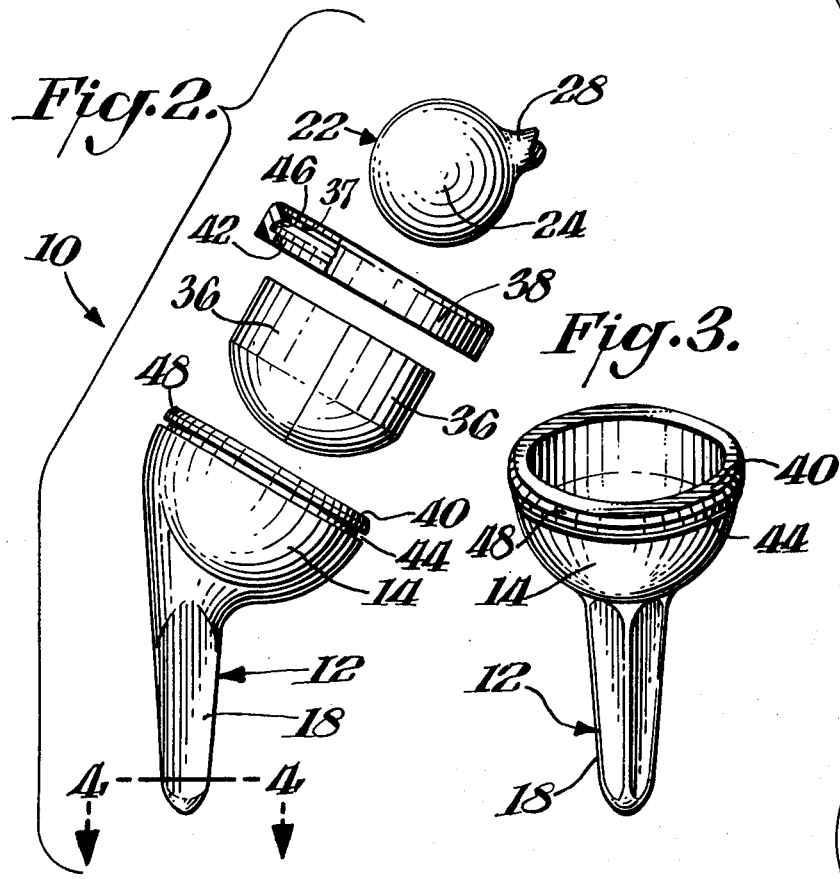
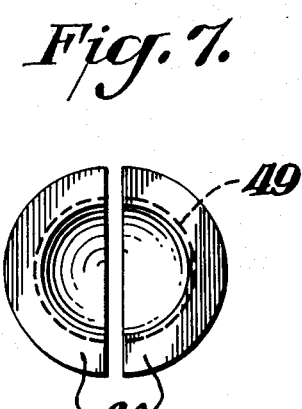
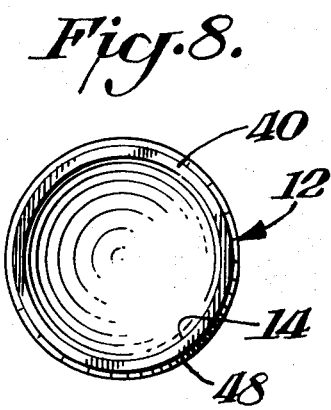

BONE AND JOINT PROSTHESIS

BACKGROUND OF THE INVENTION

Prosthesis used for joining and replacing human bones and joints necessitate a means for conveniently and reliably locking bones and joints securely together in an articulating or a nonarticulating manner. Various conventional mechanical locking devices, such as screw threads and collets, have been used, but they have the problem of releasing or backing off under prolonged service or might not be convenient for installation and removal in surgery. An object of this invention is to provide a simple and economical prosthesis for locking joints and bones together, and more particularly, to such a prosthesis which facilitates the installation and removal of articulating prosthetic joints in the human body.

SUMMARY

In accordance with this invention, the ball carrying scapular component is rotatably held within the cup of the humeral component between a pair of split plastic lining inserts, which are locked within the cup by a resilient plastic lock ring, which snaps into an external circular groove on the rim of the socket. The rim and lock ring may have mutually engaging bevelled edges which firmly engage each other. The split lining inserts are, for example, made of ultra high molecular weight polyethylene. The humeral and intracancellar components are, for example, made of a biocompatible metal, and the insert liners are made, for example, of ultra high molecular weight polyethylene, which lends strength and self-lubrication to the joint.

BRIEF DESCRIPTION OF THE DRAWINGS

Novel features and advantages of the present invention will become apparent to one skilled in the art from a reading of the following description in conjunction with the accompanying drawings wherein similar reference characters refer to similar parts and in which:

FIG. 1 is a front view in elevation partially broken away in cross-section of a scapular prosthesis with human body portions and an extreme opposite position shown in phantom outline;

FIG. 2 is an exploded view of all of the components of the prosthesis shown in FIG. 1 with a portion of the ball component broken away;

FIG. 3 is a right side elevational view of the humeral socket portion of the prosthesis shown in FIGS. 1 and 2;

FIG. 4 is a cross-sectional view taken through FIG. 2 along the line 4—4;

FIG. 5 is a right side view of the fixation portion of the intracancellar component of the prosthesis shown in FIG. 1;

FIG. 6 is a top plan view of the locking ring of the prosthesis shown in FIGS. 1 and 2;

FIG. 7 is a top plan view of the linear inserts of the prosthesis shown in FIGS. 1 and 2; and FIG. 8 is a top plan view looking down at the cup cavity of the humeral component shown in FIG. 3.

DESCRIPTION OF THE PREFERRED EMBODIMENTS

In FIG. 1 is shown a scapular articulating joint prosthesis 10 including a humeral component 12 having a cup 14. Humeral component 12 is attached to the top of humerus 16 by insertion of tapered stem 18 having substantially triangular cross-section shown in FIG. 4, into the intramedullary canal 20 of the humerus. Humeral or socketed component 12 is made of a biocompatible metal such as cast Vitallium alloy. The centerline 15 of cup 14 and centerline 19 of stem 18 are disposed, for example, at an angle B of about 30° relative to each other.

Vitallium is the trademark of Howmedica Inc., for a special cobalt-chromium alloy developed and used for cast partial and full dentures, and for internal applications by surgeons. Cobalt and chromium constitute over 90% of its composition. Sp.gr. 8.29; tensile strength, 95,000 lb./sq.in.min.: 2% offset yield strength 65,000 lb./sq.in.min.: Reduction of area 8% min.; elongation, 8% min. modulus of elasticity, 30–32 million lb./sq.in. When polished, it is exceedingly smooth and permanently lustrous. Its outstanding qualities are clinical inertness in relation to living tissues and high degree of resistance to corrosion.

FIG. 2 shows the separate components of prosthesis 10, which are shown assembled in FIG. 1. Ball or scapular component 22 is also made, for example, of a biocompatible metal, such as cast Vitallium alloy, and includes polished spherical ball 24 connected to fixation plate 26 by neck 28. Fixation rods 30, 32 and 34 extend at strategic angles from fixation plate 26, as shown in FIGS. 1 and 5. The length of rods, 30, 32 and 34 are, for example, 15, 10 and 20 mm. The fixation means may be diversely shaped and adapted for the particular portion of the body to which ball component 22 is to be attached. Ball 24 is rotatably locked to humeral component 12 by engagement between a split pair of insert liners 36 made, for example, of high density polyethylene and more particularly of ultra-high molecular weight polyethylene, which has excellent strength and self-lubricating properties with respect to cast Vitallium alloy ball 24.

Split retaining insert liners 36 embrace ball 24 and then are locked within cup 14 under shoulder 37 of lock ring or apertured cover 38, shown in FIG. 6, which is snap fitted as shown in FIG. 1 over the outer rim 40 of cup 14. Inner flange 42 of cover ring 38 is inserted into and locked within circular groove 44 about the outer rim of cup 14. Inner bevelled ridge 46 within ring 38 has an angle of approximately 31°, which closely engages contacting bevelled rim 48 about the outer edge of cup 14, which rim 48 has an angle of approximately 33°. The angular variation between the bevelled ridge 46 and bevelled rim 48 insures a tight lock when flange 42 of cover 38 is snapped into circular groove 44. Locking cover or ring 38 is conveniently formed of a tough and resilient polyethylene, which is biocompatible as well as strong, tough, resilient and durable.

The reentrant engagement of greater than hemispherical socket 49 within liner inserts 36 about polished ball 24 securely maintains ball component 22 securely engaged within humeral component 12. For joint 10, the engagement is articulating, which allows mutual rotation in the plane shown in FIG. 1 at an angle A of approximately 90°. Similar rotations are afforded in other plans. The degree of rotation depends upon the type of joint such as shoulder, hip or elbow and in some instances, no articulation is necessary and the joint is essentially nonrotating.

Typical dimensions of the principal components of joint 10 are as follows:

| Component | Millimeters |
| --- | --- |
| Ball 24 and socket 49 radius | 11 mm. |
| Inside radius of cup 14 and outer radius of liner insert | 17.5 mm. |
| Depth of cup 14 and liner insert 36 | 21.4 mm. |
| Thickness of cup wall | 3.9 mm. |
| Outer diameter of locking cover 38 | 42.5 mm. |
| Inside diameter of locking flanges 42 at bottom of cover | 36 mm. |
| Thickness of locking flange 38 | 2.69 mm. |
| Distance between locking flange bevels 46 and inside shoulder | 2.0 mm. |
| Angle of bevel 46 within cover and on rim of cup | 31°<br>33° |
| Overall height of cover 38 | 7.15 mm. |
| Length of stem 12 | 40 mm. |
| Width of stem tapers to an end width of about | 6.4 mm. |
| Stem rear wall angle | 3° |
| The cross-section of the stem is triangular as shown in FIG. 1 with broken corners and width at section cutting line 4 is | 6.4 mm. |
| Angle of ball stem 28 to fixation plate 26 | 15° |

The prosthesis 10 is assembled in the scapular portion in the body in the following manner. The metal humeral portion 12 with an integral attached cup configuration is inserted into the intramedullary canal of the humerus bone in the upper arm after proper preparation. The scapular component 22 having a spherical ball 24 and appropriate attachments to the ball is inserted into the intracancellar portion of the scapula (upper portion of the shoulder joint).

The ultra high molecular weight polyethylene locking ring 38 is placed over the ball of the scapular component with the locking feature facing toward the open end of the humeral cup 14. The two polyethylene components 36 which form the cup shaped inserts are placed over the ball 24 of the scapula component and partially encompass the ball. This is followed by placement of the assembly into the cup portion 14 of the metal humeral component 12. The polyethylene lock ring 38 is then pressed onto the outer rim of the humeral cup component to engage in the circular slot 44 provided therefor.

I claim:

1. A prosthetic device comprising a cup-shaped component having a cup, fixation stem means extending from the base of the cup-shaped portion for attaching it to a boney portion of the body, a ball component, fixation rod means connected to the ball component for connecting it to another boney portion of the body, a split lining insert means having outer dimensions contructed and arranged for engagement within the cup, the split lining insert means having an inner cavity constructed and arranged for reentrantly embracing the ball, an internally flanged locking ring for engaging the outer rim of the cup, the internally flanged locking ring having an aperture through which the ball component is freely inserted, a circular groove above the rim of the cup for snugly receiving the internal flange of the locking ring, and a retaining shoulder within the locking ring for retaining the insert liners and ball within the cup.

2. A prosthetic device as set forth in claim 1 wherein the ball is substantially spherical and the cavity within the split insert liner means is slightly greater than hemispherical.

3. A prosthetic device as set forth in claim 2 wherein the fixation stem means of cup-shaped component is constructed and arranged for engagement within the intramedullar canal of the humerus, and the fixation rod means on the ball component is constructed and arranged for engaging the intracancellar portion of the shoulder.

4. A prosthetic device as set forth in claim 1 wherein the split lining insert means comprises ultra high molecular weight polyethylene, and the cup-shaped and ball components are biocompatible metal.

5. A prosthetic device as set forth in claim 1 wherein the angle of rotation between the cup-shaped and ball components is approximately 90°.

6. A prosthetic device as set forth in claim 1 wherein the cup-shaped component and fixation stem means attached thereto have centerlines and the centerlines are disposed at an angle of 30° relative to each other.

7. A prosthetic device as set forth in claim 1 wherein the fixation rod means comprises a fixation plate having a plurality of rods extending therefrom in a direction remote from the ball, the ball being attached to the side of the fixation plate opposite the fixation rods by a neck, and the neck being disposed at an angle of approximately 15° with respect to the fixation plate.

8. A prosthetic device as set forth in claim 7 wherein the fixation rods extend from the fixation plate to lengths of approximately 10, 15 and 20 mm.

9. A prosthetic device as set forth in claim 1 wherein the fixation stem means is constructed and arranged for insertion in the intramedullary canal in the humerus, and the fixation rod means is constructed and arranged for affixation to the scapular portion of the body thereby constituting the prosthetic device for replacement of a shoulder joint.

10. A prosthetic device as set forth in claim 9 wherein the cup-shaped component has a centerline, the fixation stem means having a centerline, said centerlines being disposed at an angle of approximately 30° relative to each other, and one side of the fixation stem means being substantially tangent to the outer surface of the cup-shaped component.

11. A prosthetic device as set forth in claim 1 wherein the fixation stem means is substantially triangular in cross-section.

12. A prosthetic device as set forth in claim 1 wherein the rim of the cup and the contacting ridge within the locking ring are correspondingly bevelled for close engagement therebetween.

13. A prosthetic device as set forth in claim 12 wherein the angle of bevel of the rim of the cup is slightly greater than the angle of bevel of the ridge.

14. A prosthetic device as set forth in claim 13 wherein the rim is bevelled at an angle of approximately 33° and the ridge is bevelled at an angle of approximately 31°.

\* \* \* \* \*